United States Patent [19]

Greenwalt et al.

[11] Patent Number: 4,685,314
[45] Date of Patent: Aug. 11, 1987

[54] DEVICE AND METHOD FOR PREVENTING TRANSFUSION OF INCOMPATIBLE BLOOD

[75] Inventors: Tibor J. Greenwalt; Norman A. Coe, both of Cincinnati, Ohio

[73] Assignee: University of Cincinnati, Cincinnati, Ohio

[21] Appl. No.: 708,707

[22] Filed: Mar. 6, 1985

[51] Int. Cl.⁴ ............................................. E05B 65/00
[52] U.S. Cl. ............................................ 70/57; 70/19
[58] Field of Search ................... 70/19, 57, 58; 604/4, 604/6, 7, 48, 110

[56] References Cited

U.S. PATENT DOCUMENTS 1,343,847  6/1920  Reid ........................................ 70/19
1,376,049  4/1921  Stretch .................................... 70/19

FOREIGN PATENT DOCUMENTS 359156  1/1906  France ..................................... 70/57

Primary Examiner—Robert L. Wolfe
Attorney, Agent, or Firm—Frost & Jacobs

[57] ABSTRACT

A device and method for preventing transfusion of incompatible blood comprises a means for performing the following procedures. Upon admission to the hospital, a rapid blood type test is performed in the presence of the patient and, immediately thereafter, a wrist band with a key or other releasing means corresponding to the patient's blood type is secured to the patient's wrist. A locking mechanism is provided on all blood bags in the blood bank at the time of the blood donation which corresponds to the blood type contained in the bag and is color coded. Blood is dispatched from the blood bank for a patient upon request after the usual crossmatching. Upon arrival at the patient's location, the bag is unlocked using the key attached to the patient's wrist band and the blood transfusion is administered.

11 Claims, 4 Drawing Figures

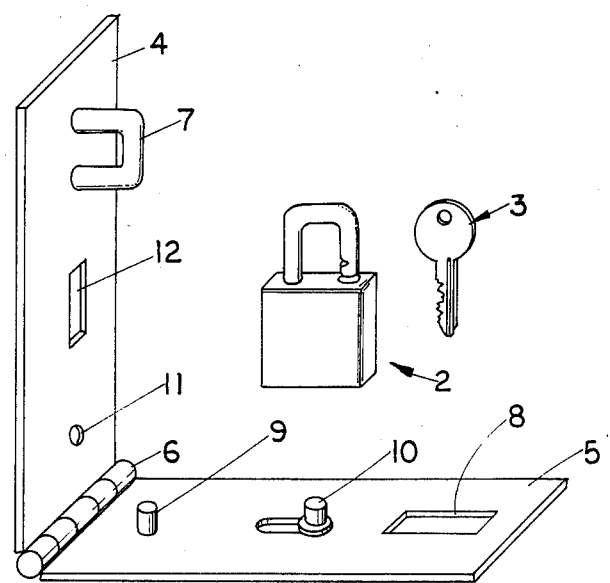
FIG. 1
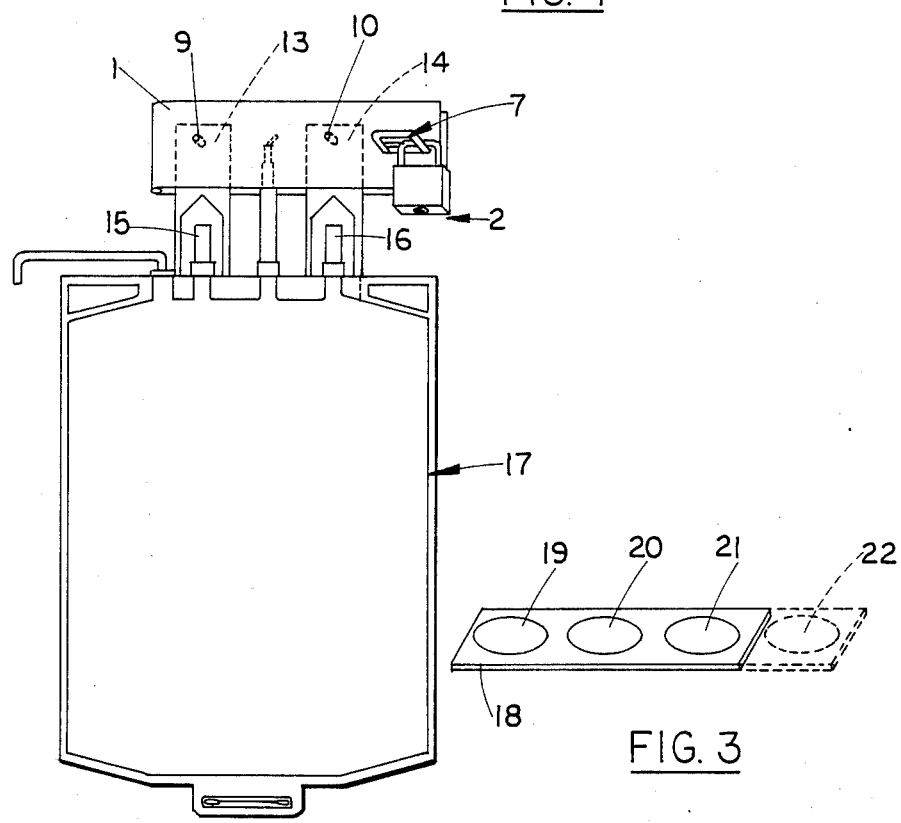
FIG. 2
FIG. 3

BLOOD IS:   A        B      Rho(D)   A,B
           BLUE    YELLOW

O, Rh neg.

O, Rh pos.

A, Rh neg.

A, Rh pos.

B, Rh neg.

B, Rh pos.

AB Rh neg.

AB, Rh pos.

DEVICE AND METHOD FOR PREVENTING TRANSFUSION OF INCOMPATIBLE BLOOD

BACKGROUND OF THE INVENTION

1. Field of the Invention

This invention relates to a means for identifying blood types and preventing transfusion to a patient of a blood type incompatible with the blood of the patient. The device and method minimize the possibility of error in the retrieval, storage and subsequent transfusion of blood.

2. Description of the Prior Art.

(a) Patents.

Transfusion to a patient of blood which is incompatible with the blood type of that patient can cause a serious reaction and is sometimes fatal. The prior art teachings aimed at preventing that problem include U.S. Pat. Nos. 4,265,101 and 4,302,956 which describe devices designed to guard against the most frequent cause of incompatible blood transfusions—clerical errors.

U.S. Pat. No. 4,265,101 teaches a "holder bag" adapted to hold a bag of blood. The holder bag is completely sealed except for a locking cap. The locking cap operates much like a combination lock. The proper combination to release the cap, according to the teachings of this patent, is established by a blood bank technician at the time a pre-selected bag of blood is placed in the holder bag and dispatched from the blood bank to the patient's location. The blood bank technician sets the combination of the locking cap to correspond to the patient's identification number assigned at the time of admission to the hospital. Upon the arrival of the blood bag to the patient's location, the staff member who administers the transfusion must obtain the patient's identification number from the patient's wrist band and enter that number into the locking cap. The cap is thereby released and the staff member obtains access to the pre-selected blood bag.

U.S Pat. No. 4,302,956 teaches an improvement upon the holder bag patent. This patent teaches a different locking mechanism suitable for use with blood bags of the type having a lockable flap. The teachings of U.S. Pat. No. 4,302,956 are nearly the same as those of U.S. Pat. No. 4,265,101 except that a different mechanism is used for locking the pre-selected blood bag just prior to dispatch from the blood bank. Like the U.S. Pat. Nos. 4,265,101, 4,302,956 teaches a locking mechanism which operates by a combination lock. The patent teaches that the combination of each individual lock is to be set by blood bank technicians to correspond to the patient's identification number at the time a blood bag is dispatched from the blood bank. Upon arrival at the patient's location within the hospital, the locking device is released by entering the patient's identification number found on the wrist band of the patient.

The devices disclosed in U.S. Pat. Nos. 4,265,101 and 4,302,956 guard against clerical error in only one portion of the blood administration cycle. The devices merely help to prevent blood which is properly selected and dispatched from the blood bank from being delivered and administered to the wrong patient. However, these devices do nothing to prevent errors in other portions of the blood transfusion cycle.

Consider a typical transfusion cycle. Before a blood transfusion can be prepared and dispatched from the blood bank, the blood type of the patient who will receive the transfusion must be determined. As taught by these patents and typically done in practice, a blood sample is taken from the patient, labelled in some manner such as by name or identification number to identify its source and transported to a blood analysis laboratory. There, a lab technician analyzes the blood sample. The laboratory technician then relays to the blood bank the blood type and other information corresponding to the patient's name or other identifying characteristic such as the patient's identification number. The blood bank technician then selects a bag containing the appropriate blood type. At this point in the process, one of the locking devices of the above-described patents is used. The blood bank technician sets the combination to correspond to the identification number of the patient and dispatches the locked blood bag to the patient's location. Upon its arrival, the nurse unlocks the blood bag and administers the transfusion. It is obvious that only a portion of the cycle is benefitted by the devices disclosed in the above mentioned patents. They do nothing to prevent clerical errors between the time that the blood sample is drawn from the patient and the time that a blood bag is selected to be sent to the patient. It is an object of the present invention, therefore, to provide more complete protection and guard against clerical errors throughout the entire process.

(b) Non-Patent Prior Art.

Another item of prior art widely in use is a system distributed by Hollister Incorporated known as the "Ident-A-Blood Recipient System". The Ident-A-Blood System consists of labels and forms which are used according to a prescribed procedure. If the labels and forms are used in accordance with the procedure, the Ident-A-Blood System helps minimize the likelihood of clerical errors. The system does not contain any distinctive mechanisms or devices; it consists only of labels and forms.

The Ident-A-Blood System is not easy to explain. However, the Ident-A-Blood System is described in the following quote from a June 1977 article published in *Laboratory Medicine* entitled "A Positive Blood Recipient Identification System In A General Hospital":

"How The System Works

At the time a transfusion is requested, a transfusion requisition form with an attached sheet of blood tabs and armband containing the key transfusion number is completed. The number of units required plus pertinent clinical information is filled in. For each unit of blood requested, a crossmatch transfusion report is imprinted with the patient's name.

Blood is drawn from the patient after carefully verifying the patient's identification. At this time, the armband, at the bottom of the blood tab sheet, with the key identification number, patient's name, date, and time the blood was drawn is placed on the patient. The tube of blood is labeled with the appropriate specimen tube label also containing the key transfusion number. The blood sample, requisition forms, and crossmatch transfusion forms are then sent to the Blood Bank.

In the blood bank, the technologist completes the typing and crossmatching procedures, labeling the test tube rack with the rack label from the blood tab sheet. At the time the crossmatch is completed, the appropriate information listing the recipient's type and the crossmatch reactions is filled in on the crossmatch transfusion report form. Labels containing the key identification number from the blood tab page are placed on all copies of the crossmatch transfusion reports. The blood unit identification tabs containing the key identification number are then placed on the correct units.

The units available for transfusion are listed on the chart copy of the transfusion requisition form by number and this is then placed on the patient's chart. The identification copy (green) from the crossmatch transfusion form is placed in a "Transfusion Ready" box at the door of the blood bank.

When the ward personnel come to pick up the blood, using appropriate identification, they select the identification forms and present those to the blood bank technologist. The technologist then matches the identification form with the correct unit of blood. The person issuing the blood as well as the person receiving the blood sign the crossmatch transfusion report form, which accompanies each unit.

At the time of starting transfusion, the patient is re-identified, both verbally and visually. The key transfusion numbers are correlated on the patient's armband, on the crossmatch transfusion report forms, and on the units of blood. These key transfusion numbers must agree before the blood transfusion can be started.

Temperature, pulse, and blood pressure are recorded on the crossmatch transfusion form before starting the blood and the patient is carefully observed during the first few minutes of transfusion. Temperature, pulse, and blood pressure are checked again and recorded one hour after starting the blood. The times the transfusion is started and completed are recorded on the transfusion report form. Should any reactions develop, the transfusion is stopped and appropriate procedures for investigating such reactions are instituted, including a recheck of the patient's identification."

While the Ident-A-Blood System described above contains many advantages over no system at all, several disadvantages have been recognized. Some of these disadvantages are described in the following quote from the same article:

"Disadvantages

Several difficulties and problems were pointed out also by the staff and technologists:
1. The extra paper work for the ward personnel, and particularly for the technologists, increased the amount of time involved in crossmatching and transfusing patients. The system initially was thought to be fairly complex when instituted. However, after it had been used for a while, both the extra paper work and the complexity seemed to be only minor problems.
2. The armbands have presented some problems on certain patients. Patients who are receiving large amounts of blood often accumulate several armbands during a short period of time, making it difficult to find room for a new armband and also to find the appropriate armband when a unit of blood is administered. Furthermore, since the armbands are removed after 24 hours, occasionally errors are made and the wrong armband is removed.
3. *Probably the most serious problem with the system is that it often is not followed completely, and there is no effective way of insuring that it is followed.* The most common error is that a member of the house staff will draw the blood, take the tube to the nurse on the ward, ask her to label the tube, and go back and put the armband on the patient. This obviously defeats the purpose of the system and allows for errors to arise.
4. A minor problem occurs when more than four units are crossmatched on a single tube. Since the forms provide key transfusion numbers for just four units, blank tabs are filled in with the appropriate key transfusion number in the blood bank, if more than four units are to be crossmatched. Having to write in these numbers provides another possible source of error.

Before the Hollister System was begun, errors in patient identification seemed to arise quite commonly, although we could not document the exact frequency. The following brief case reports describe several situations in which identification errors have occurred.

Reports of Errors While Using Hollister System

Case 1: A 41-year-old woman was struck by a car and was brought to the emergency room unconscious. After administration of fluids and blood she became more responsive. She was found to have extensive hip fractures and evidence of bladder rupture. This was repaired surgically. Following surgery, it was thought that she still needed blood replacement.

One unit she was to receive had a donor number 17J61673. Inadvertently, the technologist took 17J61763 which was the same type as the patient (A+). When she noticed the key transfusion number was missing, she thought that this had been omitted by mistake and manually wrote out another tag to place on the unit. This unit was released and administered to the patient without difficulty. When the error was noted, the unit was crossmatched and found to be compatible.

Case 2: A 45-year-old woman had two units of blood crossmatched for routine hysterectomy. When the blood was sent to surgery, the technologist transposed two numbers in an eight-digit donor number, similar to the error made in Case 1. One of the two units released was uncrossmatched, but ABO and Rh compatible. Although this unit lacked the key transfusion number, neither the person issuing nor the person picking up the blood noticed this omission.

The unit soon was missed in the blood bank, the error realized, and the unit recovered from the operating room before being administered to the patient. Had the unit been needed, we would hope that the person administering the blood would have noticed that the key transfusion number was missing from the unit and would not have given it.

Case 3: A 24-year-old man (P. B.) was admitted for extensive second and third degree burns. His early treatment included intravenous fluids and whole blood. An intern drew blood from the patient for crossmatch, put the correct armband on the patient, but handed the blood to the ward secretary to label. She imprinted the label with another patient's name (D. M.), put the label on the tube and sent it to the blood bank. Since P. B. and D. M. previously had been typed and were different ABO types, the discrepancy was detected at the time of crossmatching and a correctly labelled tube was obtained from P. B.

Had the patients been the same ABO and Rh type, the error would have been detected at the time of attempted administration to D. M., since P. B. and not D. M. had on the corresponding armband.

Case 4: An elderly man (J. S.) was admitted for TUR. The evening before surgery, the on-call intern who did not know the G.U. patients was called to draw the crossmatch tube. The forms were correctly filled out, but unfortunately he did not verify identification with the patient and drew blood from G. T. instead. T. G. received the armband intended for J. S. Fortunately, both T. G. and J. S. had previously been typed and had different ABO types. A sample was then correctly obtained from J. S. Again, if the error had not been detected in the laboratory, J. S. would not have received the wrong unit of blood in surgery, since he would not have had on the corresponding armband.

In all four situations where errors in patient identification occurred, the errors never would had arisen if the system had been followed rigidly. We believe that the system is well designed and has the capability of significantly reducing identification errors even in a busy general hospital with a large number of house staff members.

The problem with the system obviously centers around unwillingness or failure of the staff to follow the system completely. *It is ineffective and no better than other systems if the entire system is not followed from start to finish.* (Emphasis added.)"

Note that the patent and non-patent prior art teachings described above call for identification of the blood type by a sample drawn from the patient and delivered to a laboratory. All subsequent transactions leading ultimately to the transfusion of blood to the patient are dependent upon properly analyzing the blood sample and correlating the results to the individual patient's identity by name or hospital ID number. Also, the prior art, particularly the Ident-A-Blood System, relies upon proper visual verification at several steps in the process. It is an object of the present invention to minimize such opportunities for error. It is also an object of the present invention to provide an improved device and method for prevention of mistranfusion of ABO or Rh incompatible blood.

SUMMARY OF THE INVENTION

The present invention provides a device and method for closing the identification loop necessary to link blood products to patients. Upon admission to the hospital, each patient is administered a simple test using anti-A, anti-B and other sera which determines the ABO and Rh group of the patient. This test is performed by a member of the admissions staff who, in the presence of the incoming patient, interprets the results. As an added security precaution, the test interpretation may be reconfirmed by the blood bank personnel after admission.

After the test is completed and the incoming patient's blood type has been determined, a wrist band corresponding to the patient's blood type is secured to the patient's wrist. Affixed to the wrist band, is a key or other device suitable for releasing a lock.

Under the method of the present invention, all blood bags in the blood bank are provided with a color coded locking mechanism of the present invention at the time of issue. With this mechanism in place, blood can not be drawn from the blood bag until the lock is released. The locking mechanisms are color coded to correspond with the type of blood contained in the bag.

When blood is ordered for a patient under the method of the present invention, the donor blood is crossmatched following usual laboratory crossmatching procedures and the blood bag with a lock attached is dispatched from the blood bank. Upon arrival at the patient's location, the person who administers the transfusion first must release the lock using the key attached to the patient's wrist band. For the key to properly operate, it must be a key selected from the set which corresponds to the type of blood contained in the blood bag. The person administering the transfusion has little choice but to use the key on the patient's wrist. It is not possible for them to ignore the protective system as can be done with prior art systems. Furthermore, the system calls for blood typing and tagging of the patient immediately upon admission to the hospital. This minimizes the mislabelling or mishandling of patient blood samples as described in the article quoted above. In effect, the present invention closes the identification loop on donated blood type and an incoming patient's blood type thereby preventing mistransfusions of ABO or Rh incompatible blood.

DESCRIPTION OF THE DRAWINGS

FIG. 1 is a perspective view of the locking assembly of the present invention.

FIG. 2 is an illustration of the locking assembly secured to a typical blood bag.

FIG. 3 is an illustration of the test card used with the present invention.

DESCRIPTION OF THE PREFERRED EMBODIMENT

Figure 4:
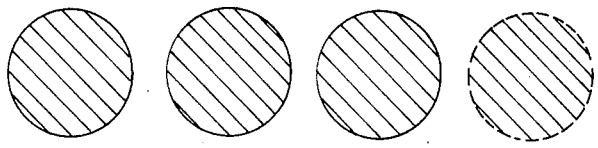
FIG. 4 is an illustration of the reference card used with the present invention.
Figure 4:
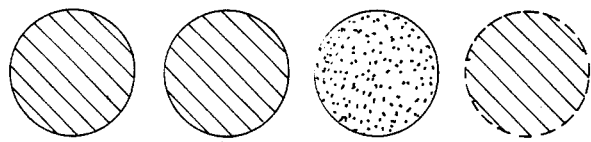
Figure 4:
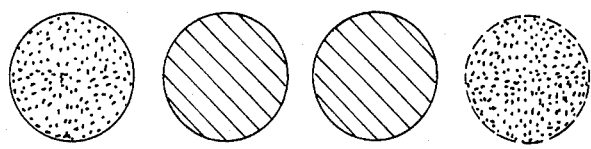
Figure 4:
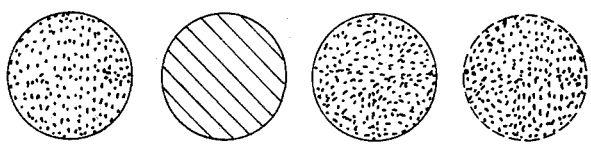
Figure 4:
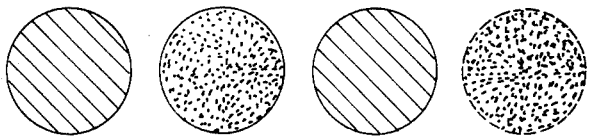
Figure 4:
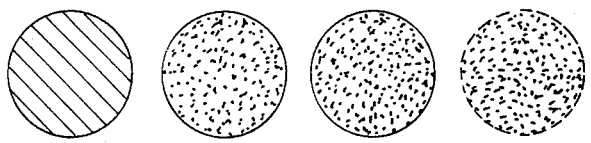
Figure 4:
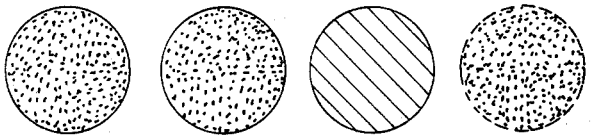
Figure 4:
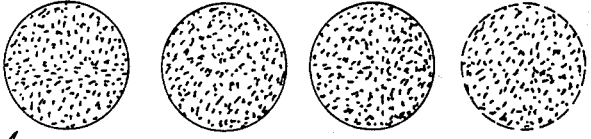

FIG. 1 illustrates the locking assembly of the present invention. The locking assembly consists of a hasp 1, a lock 2 and a key 3. As shown, the hasp is in an open position. When moved into a closed position, hasp 1 may be secured in its closed position by lock 2.

Hasp 1 consists of two rectangular planar members, 4 and 5, pivotally joined along one edge by a hinge 6. A staple 7 is attached to the interior surface of one of the members, 4 or 5, and is positioned such that when the planar members 4 and 5 of the hasp 1 are moved toward each other and into a closed position, the staple 7 passes through an aperture 8 which extends through the opposite one of the planar members, 4 or 5.

Also attached to one of the planar members 4 or 5 of hasp 1 are pins 9 and 10. Pins 9 and 10 may be rigidly attached to the planar member 4 or 5 or may be slidably mounted to the planar member 4 or 5 to allow the distance between pin 9 and pin 10 to be varied. Pins 9 and 10 may be of any cross section design and an appropriate length and position to protrude at least slightly into apertures 11 and 12 located in the planar member 4 or 5 opposite the planar member to which pins 9 and 10 are secured.

Lock 2 may be a conventional padlock or any other suitable locking device. All that is required of the lock is that it be suitable for retaining the hasp in a closed position. This function is obtained from padlock 2 by hooking the padlock through staple 7 and snapping the padlock shut. One skilled in the pertinent art will recognize that the functions of the hasp 1 and the lock 2 may be achieved in numerous ways.

FIG. 2 illustrates the hasp 1 and lock 2 applied to a typical blood bag. As shown in that illustration, a typical blood bag has two access flaps 13 and 14. These flaps each consist of two mating panels which must be peeled apart to obtain access to spouts 15 and 16 which access the blood in blood bag 17. As shown in FIG. 2, the locking assembly prevents access to the contents of blood bag 17 by retaining in a closed position the mating panels of flaps 13 and 14.

The locking assembly works as follows. Pins 9 and 10 are positioned to engage apertures extending through flaps 13 and 14. Pins 9 and 10 also extend further to engage the apertures located in the opposite planar element 4 or 5. The padlock 2 is closed through the staple 7 to secure the hasp 1 in a closed position. Under this condition, the blood bag contents can be withdrawn only (1) by releasing lock 2 and disengaging the hasp from the flaps 13 and 14 so that their mating panels may be peeled back to expose tubes 15 and 16 or (2) by forcibly removing the flaps 13 and 14 to expose tubes 15 and 16. It is evident, therefore, that a nurse or technician who lacks an appropriate key could not accidently use the contents of a blood bag.

For the locking assembly of the present invention to be effective, it is essential that each blood bag receive an appropriate lock and that each patient receive an appropriate key. To maximize the accuracy of these allocations it is imperative to distribute the lock and key immediately after the blood has been analyzed and while the donor or patient is still present. The present invention requires this procedure and provides a means for its implementation.

FIG. 3 illustrates a test card 18 used for evaluating the blood type of incoming patients upon admission to the hospital. The card is embossed or otherwise marked to establish at least three discrete sample regions, 19 through 21. Region 19 is intended to contain anti-A reagent, region 20 is intended to contain anti-B reagent, and region 21 is intended to contain anti-Rh$_O$(D) reagent. An optional region 22 may be added to contain anti-A,B reagent. The regions can be made to contain the proper reagents either by placing a small quantity of the appropriate reagent in the corresponding region with a conventional pipet or the like just before use or by producing a card on which the reagent is microencapsulated.

FIG. 4 illustrates a reference card 23. This card may be used by admissions employees of the hospital or the blood bank to interpret the results of the reactions in each of the regions 19 through 21. When a small blood sample taken from a finger or earlobe is placed in each of the three regions 19 through 21, and mixed with the reagent, the blood and reagent will react in each of the fields to create a visual image which is indicative of the patient's or donor's blood type. Reference card 23 is used as a guide to provide a visual representation of the blood type of the patient or donor.

As indicated at 24 and 25, field 19 is blue and field 20 is yellow. Field 19 contains anti-A reagent and field 20 contains anti-B reagent. Because the Food and Drug Administration requires that anti-A reagents be colored blue and that anti-B reagents be colored yellow, errors of transposition can readily be detected. If the cards 18 were microencapsulated, errors could be further minimized.

The test card of FIG. 3 and the reference card of FIG. 4 are used in the hospital as follows. Upon admission to the hospital, a finger or earlobe of the incoming patient is cleaned with alcohol on a conventional cotton swab. The finger or earlobe is allowed to dry then incised with a conventional sterile lancet. A small amount of blood is transferred from the puncture site to the sample regions 19 through 21 of card using a conventional applicator stick or toothpick. The card may be made of any suitable material such as cardboard or plastic and is designed so that the necessary patient information (e.g. name, sex, hospital number, social security number and date of birth) can be entered or imprinted on the card. Each of the card regions 19 through 21 is embossed or otherwise designated as A, B, Rh$_O$(D).

Just before transferring a small amount of blood to each of the sample regions with separate individual applicators, a drop of the appropriate reagent is placed in each sample region 19 through 21 of the card 18. As mentioned above, this step in the process can be avoided if the card 18 is microencapsulated with the reagent. The blood sample is mixed with the blood grouping reagent using a spreading circular motion with each individual applicator in its corresponding region.

The reactions between the blood and the anti-A and anti-B reagents will occur rapidly. The anti-Rh$_O$(D) reaction may require incubation for two to three minutes at 37°–40° C. (98.6–104° F.) unless a reagent designed for use in a saline medium is used. In that case, one or two drops of 0.85–0.90% salt solution may be added to the anti-Rh$_O$(D) reaction region. In this manner, all the reactions will be ready for interpretation in about three minutes. An experienced person can interpret the reactions easily by comparing the visual appearance of the test card 18 to reference card 23 which illustrates the expected agglutination reactions.

As mentioned above, the A,B region 22 is optional. It is not necessary to include the anti-A,B test since the four basic blood types—A, B, A—B and O—can be detected without its use. The anti-A,B reagent and the anti-Rh$_O$(D) reagent have a similar color and easily could be transposed. Therefore, use of anti-A,B is not recommended and not considered necessary.

The items shown in FIGS. 1 through 4 are used to implement the system of the present invention. Using these items, the present invention provides a method for preventing mistransfusion of ABO and Rh incompatible blood.

The method of the present invention calls for use of the test card 18 and the reference card 23 at the time a patient is admitted to the hospital. It is essential to the method of the present invention that the blood type test be conducted in or near the presence of the patient or that some technique be employed which will ensure that each test card be attributed to the proper individual and that the individual be given a key 3, in the case of an incoming patient, which corresponds to his or her blood type. As an optional precaution, each test card, imprinted with the name of the donor or patient, can be sent to the blood bank where interpretation of the results can be verified.

In the case of an incoming patient, the admissions staff member administers the blood typing test at the same time that other admissions procedures are performed. When the patient's blood type has been determined, a key 3 corresponding to that blood type is affixed to the patient, preferably by a wrist band. The key 3 and wrist band preferably are color coded to indicate blood type.

Thereafter, the patient's blood type will be evident from his or her wrist band and key 3. If a transfusion is needed, the required units of the appropriate blood type will be ordered from the blood bank. Conventional cross match analysis will be conducted. Consequently, clerical errors leading to transfusion of ABO or Rh incompatible blood types are avoided. The blood bank will receive an order for a specified type of blood to be sent to a specified patient. Even if the order is somehow confused during the cross matching procedure or delivery, an error in ABO or Rh group will become exceedingly evident when the nurse or technician attempts to administer the transfusion. If the blood bag contents and lock do not match the blood type of the patient and the patient's wrist band and key, the nurse or technician will be unable to open the lock and access the blood bag contents. In this manner, the present invention eliminates the possibility of clerical errors which might lead to transfusion of ABO or Rh incompatible blood.

What we claim is:

1. A locking assembly for preventing mistransfusion of blood products from a container, said assembly comprising:
   a sealing means for releasably sealing a blood product container, said sealing means including at least one interlocking element which passes through a corresponding locking aperture in said container to prevent access to the contents of said container;
   a locking means for securing said sealing means in sealed position, thereby preventing withdrawal of blood products from the container; and
   a releasing means for releasing said locking means and thereby permitting withdrawal of blood products from the container, said releasing means and locking means being uniquely matched to one another and identifying an Rh group of the specific type of blood product in said container.

2. The locking assembly according to claim 1 wherein said sealing means comprises:
   a first member;
   a first pin secured to said first member;
   a second pin secured to said first member; and
   a second member having apertures extending therethrough suitable to accomodate said first pin and said second pin.

3. The locking assembly according to claim 1 wherein said releasing means and said locking means are matched to correspond only to a single Rh group of a specific blood type.

4. The locking assembly according to claim 2 wherein said first member and said second member are planar.

5. The locking assembly according to claim 3 wherein said releasing means further comprises a key.

6. The locking assembly according to claim 2 wherein said first member further comprises an aperture,
   said second member further comprises a staple, and
   said aperture and said staple are positioned to allow said staple to pass through said aperture.

7. The prevention device according to claim 6 wherein said locking means further comprises a padlock inserted through said staple after said staple has passed through said aperture.

8. The locking assembly according to claim 2 wherein the location of said second pin can be adjusted to vary the distance between said first pin and said second pin.

9. The locking assembly according to claim 2 wherein said first pin and said second pin each pass through a center line of a flap of said blood product container.

10. A locking assembly for preventing mistransfusion of blood from a blood product container, said assembly comprising:
    a sealing means for releasably sealing a blood product container, said sealing means including at least one interlocking element which passes through a corresponding locking aperture in said container to prevent access to the contents of said container;
    a locking means positioned on said sealing means for securing said sealing means in sealed position, thereby preventing withdrawal of blood products from said container; and
    a releasing means for releasing said locking means and thereby permitting withdrawal of blood products from the container, said releasing and locking means being uniquely matched to one another and identifying an Rh group of the specific type of product in said container such that said locking means may only be released by a correct match with a matching releasing means.

11. The locking assembly of claim 10 wherein said releasing means and said locking means are matched to correspond only to a specific Rh blood type.

* * * * *